United States Patent
Wu (10) Patent No.: US 10,548,774 B2
(45) Date of Patent: Feb. 4, 2020

(54) AUTO-DARKENING WELDING HELMET WITH A TOUCHABLE OPERATING SCREEN

(71) Applicant: Tecmen Electronics Co., Ltd., Nanjing (CN)

(72) Inventor: Ziqian Wu, Nanjing (CN)

(73) Assignee: Tecmen Electronics Co., Ltd., Nanjing (CN)

(*) Notice: Subject to any disclaimer, the term of this patent is extended or adjusted under 35 U.S.C. 154(b) by 275 days.

(21) Appl. No.: 15/507,699

(22) PCT Filed: Sep. 6, 2015

(86) PCT No.: PCT/CN2015/088954
§ 371 (c)(1),
(2) Date: Feb. 28, 2017

(87) PCT Pub. No.: WO2016/037545
PCT Pub. Date: Mar. 17, 2016

(65) Prior Publication Data
US 2017/0252215 A1 Sep. 7, 2017

(30) Foreign Application Priority Data
Sep. 9, 2014 (CN) .................... 2014 2 0516400 U (51) Int. Cl.
*A61F 9/06* (2006.01)
(52) U.S. Cl.
CPC ............... *A61F 9/065* (2013.01); *A61F 9/06* (2013.01); *A61F 9/067* (2013.01)

(58) Field of Classification Search
CPC .................................. A61F 9/06; A61F 9/04
See application file for complete search history.

(56) References Cited

U.S. PATENT DOCUMENTS

| | | | |
|---|---|---|---|
| 4,863,244 A * | 9/1989 | Fuerthbauer | A61F 9/067 349/14 |
| 5,751,258 A * | 5/1998 | Fergason | A61F 9/067 345/7 |
| 6,067,129 A | 5/2000 | Fergason | |
| 2006/0010551 A1* | 1/2006 | Bishop | A61F 9/06 2/15 |

(Continued)

FOREIGN PATENT DOCUMENTS

| CN | 101088481 A | 12/2007 |
|---|---|---|
| CN | 201290803 Y | 8/2009 |

(Continued)

OTHER PUBLICATIONS

State Intellectual Property Office of the P.R. China, International Search Report in International Application No. PCT/CN2015/088954 (dated Dec. 17, 2015).

(Continued)

*Primary Examiner* — Tajash D Patel (57) ABSTRACT

An auto-darkening welding helmet includes a helmet housing; a headband structure connected to the helmet housing; an auto-darkening filter provided on the helmet housing; and an adjustment device by which operating parameters of the auto-darkening filter are adjustable, wherein the adjustment device is a touchable operating screen which faces towards an operator after the operator wears the welding helmet.

18 Claims, 5 Drawing Sheets

(56) References Cited

U.S. PATENT DOCUMENTS

| | | |
|---|---|---|
| 2010/0132086 A1 | 6/2010 | Huh |
| 2013/0291271 A1 | 11/2013 | Becker et al. |
| 2014/0020147 A1 | 1/2014 | Anderson et al. |
| 2016/0125653 A1* | 5/2016 | Denis .................... B23K 9/322 |
| | | 348/90 |

FOREIGN PATENT DOCUMENTS

| | | |
|---|---|---|
| CN | 101744683 A | 6/2010 |
| CN | 101785725 A | 7/2010 |
| CN | 204050009 U | 12/2014 |
| CN | 204092330 U | 1/2015 |
| KR | 10-2012-0097653 A | 9/2012 |
| KR | 20130011710 A | 1/2013 |

OTHER PUBLICATIONS

Extended European Search Report regarding Application No. 15839748.9, dated Feb. 28, 2018, 9 pages.

\* cited by examiner

AUTO-DARKENING WELDING HELMET WITH A TOUCHABLE OPERATING SCREEN

CROSS-REFERENCE TO RELATED APPLICATIONS

This patent application is the U.S. national phase of International Patent Application No. PCT/CN2015/088954, filed Sep. 6, 2015, which claims the benefit of Chinese Patent Application No. 201420516400.3, filed on Sep. 9, 2014, which are incorporated by reference in their entireties herein.

FIELD

The present application generally relates to an auto-darkening welding helmet provided with a touchable operating screen used to various operating parameters of an auto-darkening filter of the auto-darkening welding helmet.

BACKGROUND

In order to prevent an operator from being damaged by spattering matters and various harmful rays caused by welding-arc ignition, the operator usually wears a welding helmet on his/her head before he/she carries out a welding operation.

A conventional welding helmet is usually provided with an auto-darkening filter (ADF). The auto-darkening filter generally comprises a liquid crystal panel. The liquid crystal panel is transparent in case of no welding-arc ignition. Just before the welding-arc ignition begins, the liquid crystal panel becomes opaque to protect the operator's eyes. The auto-darkening welding helmet is usually provided with a mechanically operable knob or button. Therefore, before wearing the welding helmet, the operator can set operating parameters, such as SENSITIVITY, delay time, shade, and weld mode or the like, of the auto-darkening filter by the knob or button. After the setting, the operator can wear the welding helmet on his/her head to carry out the welding operation.

This mechanically operable knob or button is generally disposed on an outer surface of a helmet housing of the welding helmet. Working environment is usually severe on welding site. When the operator wears the welding helmet to carry out the welding operation, the knob or button of the welding helmet may be most likely in contact with other workpieces or other apparatuses on site. If such contact occurs frequently, the knob or button may be damaged and thus adjustment of the auto-darkening filter will be negatively affected.

Furthermore, manipulation of the mechanically operable knob or button is relatively complex. For example, selection of a suitable operating parameter need be accomplished by first rotating and then pressing the knob or button. Such non-intuitive manipulation sometimes may increase the operator's workload.

Furthermore, if the knob or button is contacted inadvertently by the operator or the other apparatuses on site as the welding operation is being carried out, the operating parameters, which have been set beforehand, of the auto-darkening filter may be unexpectedly changed and thus the eyes of the operator may be damaged by the harmful rays.

SUMMARY

In order to solve the problems mentioned above, the present application is aimed at proposing an auto-darkening welding helmet with an improved adjustment device, by which a user can adjust operating parameters of the welding helmet's auto-darkening filer conveniently and intuitively. Further, the adjustment device is prevented from being damaged due to any inadvertent contact with it during a welding process. Furthermore, the improved adjustment device can be well protected from the inadvertent contact after the user wears the welding helmet.

In one aspect of the present application, an auto-darkening welding helmet is provided, which comprises:

a helmet housing;

a headband structure connected to the helmet housing;

an auto-darkening filter provided on the helmet housing; and a touchable operating screen used to set operating parameters of the auto-darkening filter, wherein the touchable operating screen is disposed directly adjacent to the auto-darkening filter such that an operator can manipulate the touchable operating screen only when he/she does not wear the welding helmet on his/her head, and the touchable operating screen faces towards the operator after the welding helmet is worn by the operator. In this way, after the operator has worn the welding helmet on his/her head, the touchable operating screen is protected by the helmet housing such that no inadvertent contact or damage will occur during a welding process. Further, the touchable operating screen enables the operator to set the operating parameters of the auto-darkening filter readily and intuitively such that experimental requirements of the operator can be reduced.

Optionally, the touchable operating screen is integrated with the auto-darkening filter. In order to renovate an existing welding helmet with an auto-darkening filter, such integration design can ensure that the welding helmet can be upgraded and modified by replacing the auto-darkening filter with the integrated auto-darkening filter only. Therefore, product upgradation can be carried out simply and at reduced costs.

Optionally, the touchable operating screen is provided on an inner surface of the helmet housing.

Optionally, the touchable operating screen is located on the rear side of the auto-darkening filter's body.

Optionally, the auto-darkening filter comprises a liquid crystal panel, and the touchable operating screen is disposed on the body such that it is spaced from the liquid crystal panel.

Optionally, the operating parameters of the auto-darkening filter which are adjustable by the touchable operating screen comprise SHADE, SENSITIVITY, DELAY TIME, WELDING TIME and operation modes such as WELD, GRIND and CUTTING. Optionally, the SHADE can be adjusted between 5 and 13 levels, the SENSITIVITY can be adjusted between 0 and 10 levels, and the DELAY TIME can be adjusted between 0 and 10 levels.

It should be understood that the operating parameters and/or the levels of the touchable operating screen are not limited to those contents cited above and can be arbitrarily altered as required.

Optionally, the touchable operating screen comprises a color display screen or a monochromatic display screen or a black & white display screen. The chromatic screen can provide distinct display for the operator, and the monochromatic or black & white display screen can lead to reduced manufacturing costs.

Optionally, the touchable operating screen is a resistance-type or capacitance-type touchable screen.

Optionally, an "unlock/lock" key is provided on the auto-darkening filter such that the touchable operating screen can be activated in a working state or locked in a sleep state by pressing the key.

In another aspect of the present application, a method for manipulating the above-mentioned auto-darkening welding helmet is provided, wherein when the welding helmet is not worn by an operator, he/she manipulates the touchable operating screen of the auto-darkening welding helmet with his/her hand so as to set the operating parameters of the auto-darkening filter of the auto-darkening welding helmet.

BRIEF DESCRIPTION OF THE DRAWINGS

The foregoing and other aspects of the present application will be well understood by the following description in combination with the attached drawings. It should be noted that the drawings are illustrated in different scales for clarity. However, this cannot be deemed to affect understanding to the present application. In the drawings.

DETAILED DESCRIPTION

In the drawings of the present application, those features having the same configuration or having a similar function are represented by the same reference numerals.

Figure 1A:
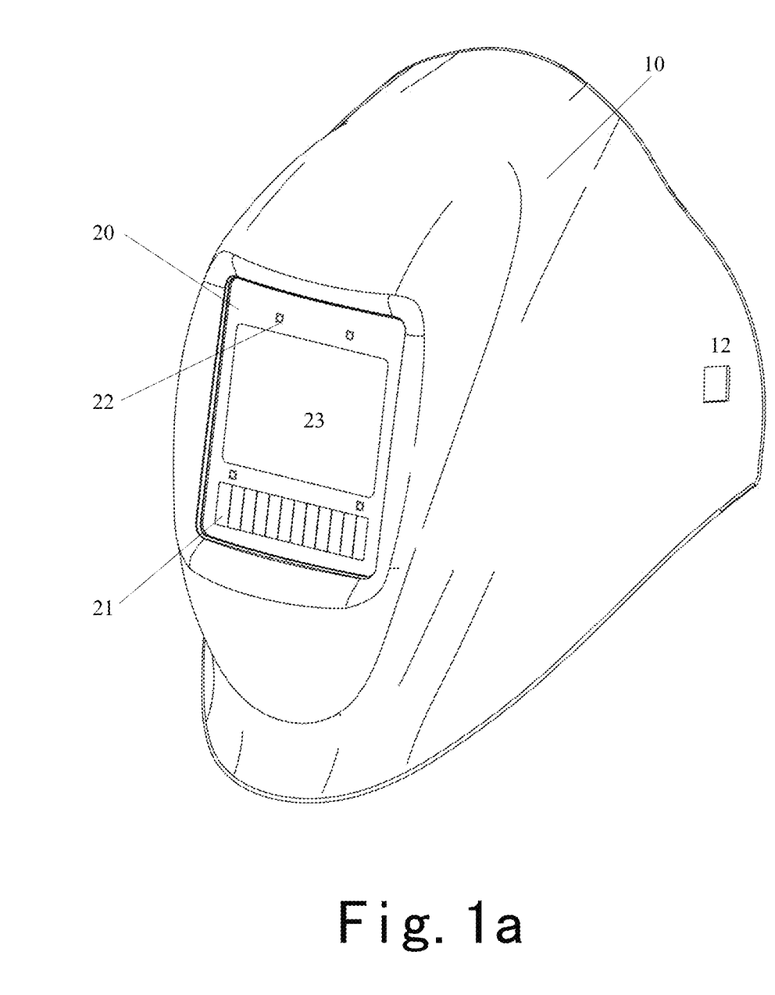
FIGS. 1a and 1b schematically show a welding helmet according to the present application in enlarged front and rear views respectively, in which the welding helmet is provided with a touchable operating screen according to one embodiment of the present application.
Figure 1B:
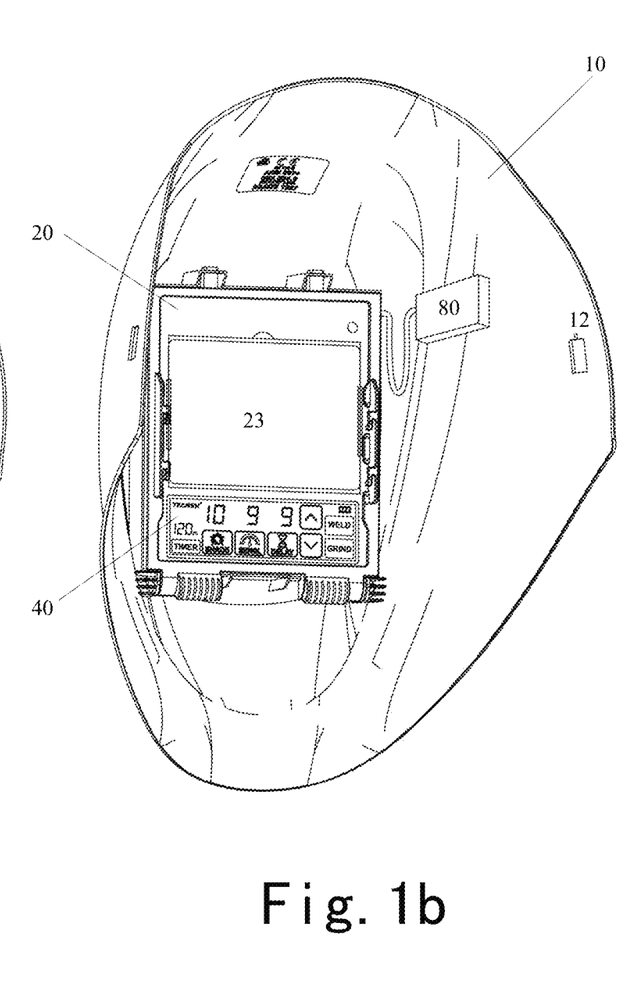
Figure 3:
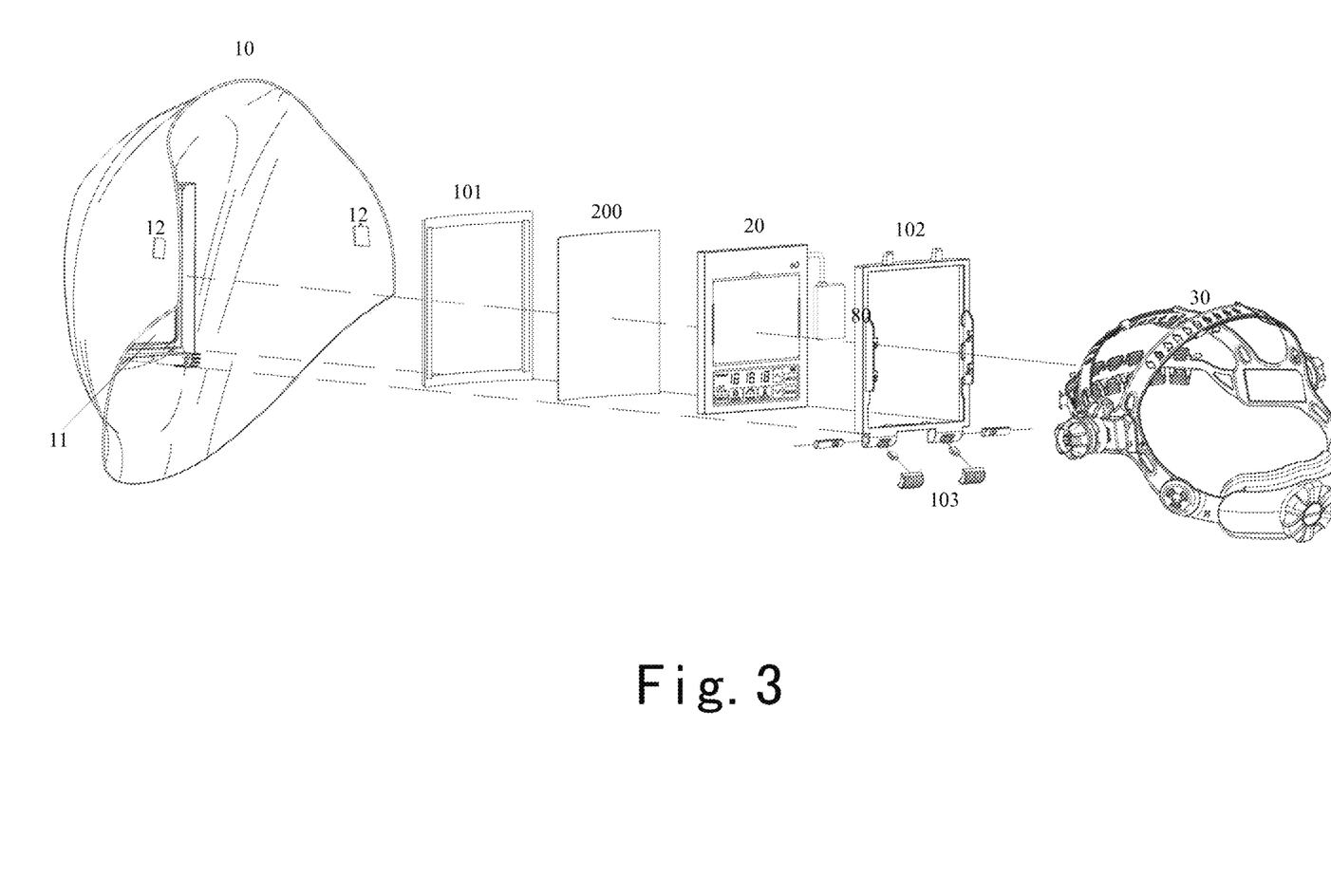
FIG. 3 schematically shows an exploded view of the welding helmet illustrated by FIGS. 1a and 1b.

FIGS. 1a, 1b and 3 schematically show an auto-darkening welding helmet according to the present application, which generally comprises a helmet housing 10, an auto-darkening filter 20 installed on the helmet housing 10 and a headband structure 30 operatively connected to the helmet housing 10. The headband structure 30 is used to be worn directly on an operator's head such that the helmet housing 10 can be secured there in place.

For clarity, the term "front face" or "front side" cited in the context of the present application refers to a face or side facing outwards and facing away from the operator's face after he/she wears the welding helmet, and the term "rear face" or "rear side" cited in the context of the present application refers to a face or side facing inwards and towards the operator's face after he/she wears the welding helmet.

As illustrated, integrated in a body of the auto-darkening filter 20 are a solar battery assembly 21, a photo-sensitive array 22, a liquid crystal panel 23 and a touchable operating screen 40 according to one embodiment of the present application. The touchable operating screen 40 can be configured to set various operating parameters of the liquid crystal panel 23, such as SENSITIVITY, delay time, shade, and weld mode or the like. Furthermore, a battery 80 can be installed on an inner surface of the helmet housing 10 to supply electric power, via electric cables, for the auto-darkening filter 20, the touchable operating screen 40 or their control circuits. It is appreciated that the battery 80 can be a rechargeable battery.

As shown in FIG. 1b, the touchable operating screen 40 is disposed directly adjacent to the liquid crystal panel 23. For example, the touchable operating screen can be disposed directly adjacent to the bottom of the liquid crystal panel 23. In an alternative embodiment, the touchable operating screen 40 can be disposed on the left or right or top of the liquid crystal panel 23. In the context of the present application, "directly adjacent to" means that only a minimum gap can be left between the touchable operating screen 40 and the liquid crystal panel 23 to reflect a boundary therebetween.

The solar battery assembly 21 and the photo-sensitive array 22 are located on the body's front face, and the touchable operating screen 40, especially its operating face, is located on the body's rear face such that after the operator wears the welding helmet on his/her head, the touchable operating screen 40 is located in the interior of the helmet housing 10 and thus is prevented from any unexpected contact with it.

As shown in FIG. 3, the auto-darkening welding helmet according to the present application comprises a transparent protective sheet 200 for protecting the auto-darkening filter 20. A first holding bracket 101, a second holding bracket 102 and a locking element 103 constitute one holding assembly. The auto-darkening filter 20 and the protective sheet 200 are removably installed in a front opening 11 of the helmet housing 10 by means of the holding assembly. Additionally, the headband structure 30 can be operatively connected to the helmet housing 10 by means of left and right openings 12 of the helmet housing 10.

Figure 2:
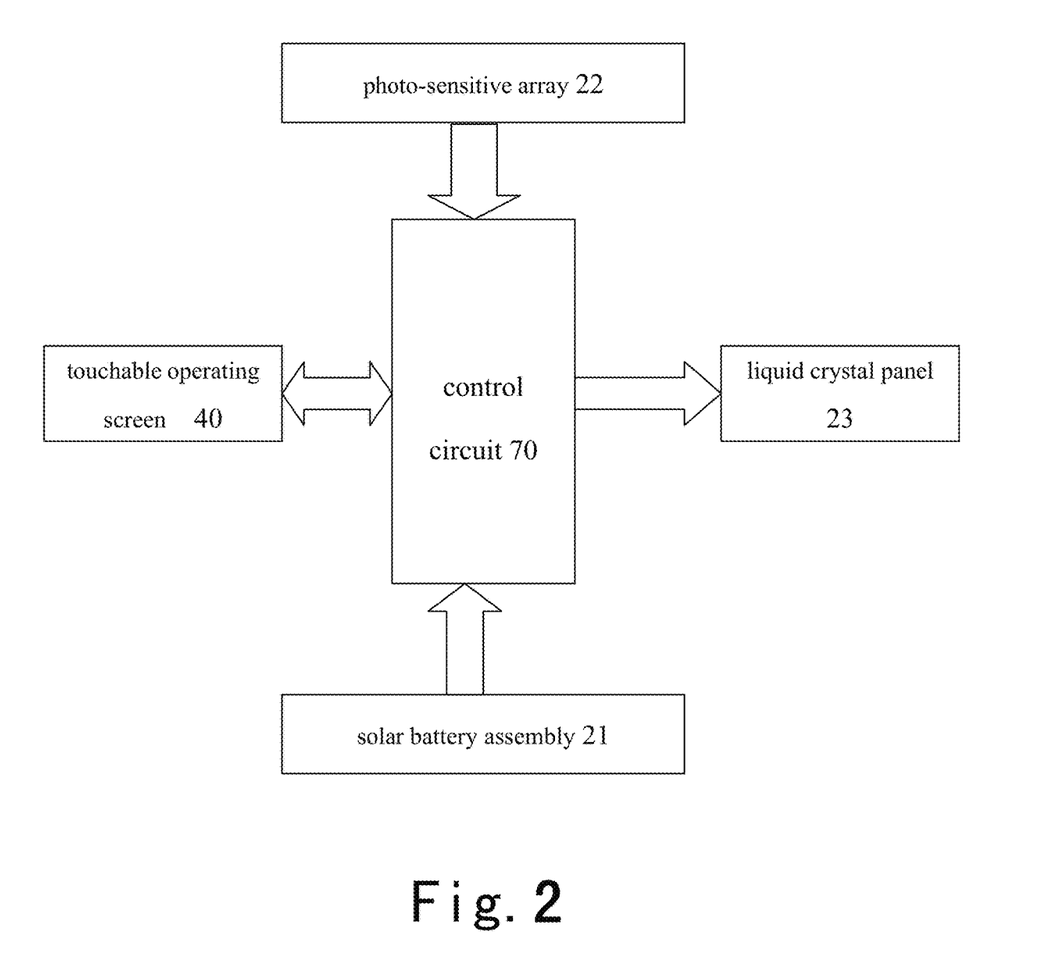
FIG. 2 schematically shows a simplified control block diagram of the welding helmet according to the present application.

FIG. 2 schematically shows a fundamental control block diagram adapted for the auto-darkening welding helmet according to the present application. A control circuit 70 of the welding helmet is in data communication with the solar battery assembly 21, the photo-sensitive array 22, the liquid crystal panel 23 and the touchable operating screen 40 respectively. Except for the touchable operating screen 40, other parts of the welding helmet can be configured in the same way as a conventional welding helmet such that the inventive welding helmet can be manufactured at costs of being not significantly greater than the conventional welding helmet. Moreover, it is appreciated that all those parts can be connected and controlled in any manner well-known by a person skilled in the art, whose explanation is thus omitted here.

It can be seen from FIG. 2 that the operator can touch the operating screen 40 by his/her finger so as to set the various operating parameters of the liquid crystal panel 23 via the control circuit 70. Unlike the prior art, the present application discards any mechanical adjustment device. According to the present application, sliding and pressing the operator's finger on the touchable operating screen 40 can enable the operator to set the operating parameters and leads to improved user friendliness and convenience.

It should be understood that the touchable operating screen 40 can be all brands of touchable screens available on the market or touchable screens customized by manufactures. The screen size of the touchable operating screen 40 can designed to be larger or smaller depending on designing requirements for the welding helmet or the auto-darkening filter. For instance, according to the principle or work, the touchable operating screen 40 may be embodied as a resistance-type touchable screen or a capacitance-type touchable screen. Further, for example, the touchable operating screen

40 may be embodied as a color display screen or a cheaper monochromatic or black & white display screen.

Figure 4A:
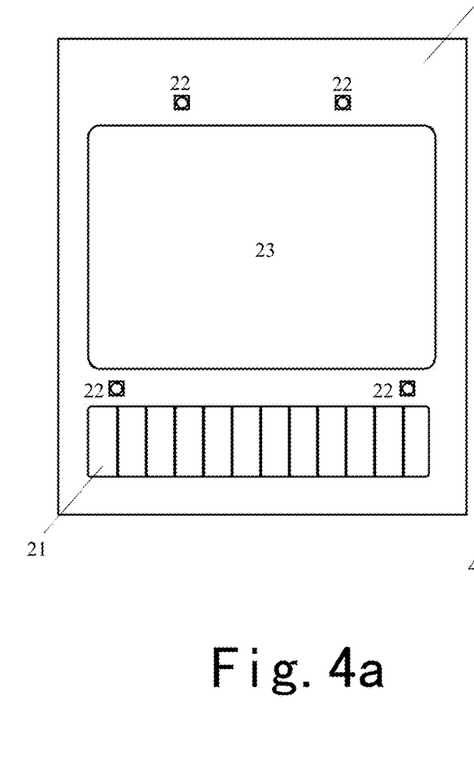
FIGS. 4a and 4b schematically show enlarged front and rear views of an auto-darkening filter equipped with the touchable operating screen illustrated in FIGS. 1a and 1b.
Figure 4B:
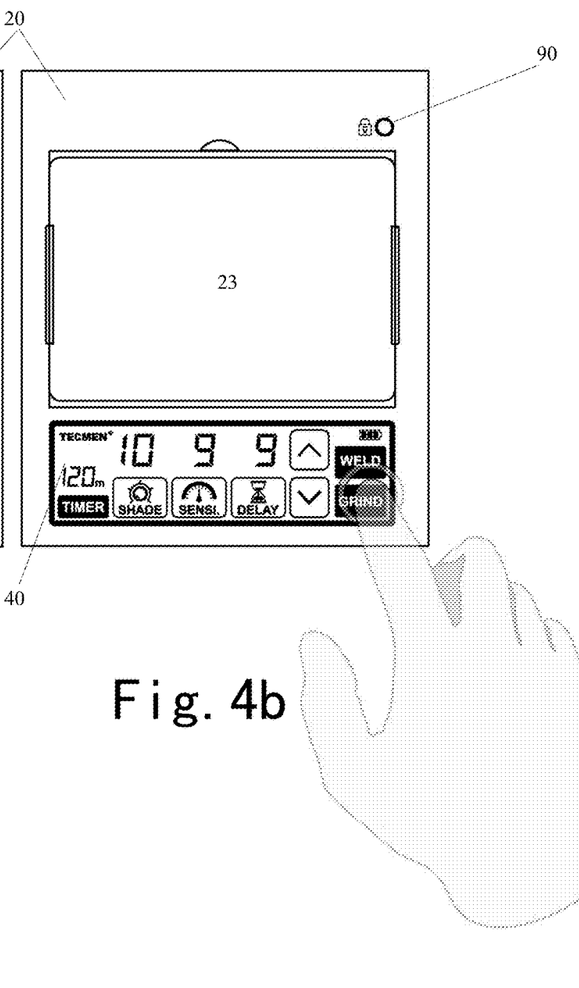

FIGS. 4*a* and 4*b* schematically show one embodiment of the touchable operating screen 40 according to the present application in front and rear views respectively. In this embodiment, the touchable operating screen 40 can be a color display screen. The touchable operating screen 40 is located on the rear side of the auto-darkening filter 20. Disposed on the same rear side is also an "unlock/lock" key 90. The key 90 is designed such that it can be pressed to unlock the operating screen before the screen is operated by the finger or to lock the operating screen in a sleep state after the operating screen is operated by the finger. In this way, an unexpected operation caused by an object (for example the face of the operator as wearing or removing the helmet) touching the operating screen can be prevented.

It can be seen from FIG. 4*b* that the touchable operating screen 40 is substantially rectangular and is disposed on the body of the auto-darkening filter 20 under the liquid crystal panel 23 such that one's finger is conveniently slidable on the touchable screen 40. It should be understood that the shape or position of the touchable operating screen 40 can be modified according to the designing requirements. For example, the touchable operating screen 40 can be alternatively designed to be disposed on the body of the auto-darkening filter 20 above or aside the liquid crystal panel 23.

Various graphics, icons or texts can be designed as necessary on the touchable operating screen 40 such that they can shine when or after one's finger touches them. For example, FIG. 4*b* shows that the touchable operating screen 40 is designed with a TIMER mark above which seconds can be displayed; a SHADE mark above which shade levels can be displayed; a SENSI. mark above which sensitivity levels can be displayed; a DELAY mark above which delay levels can be displayed; up and down adjusting arrows; operation mode marks such as WELD and GRIND; and a battery level indicating mark.

According to the present application, the SHADE is designed to be adjustable between 5 and 13 levels, the SENSI. is designed to be adjustable between 0 and 10 levels; and the DELAY is designed to be adjustable between 0 and 10 levels. Furthermore, the TIMER is designed to set welding time.

For example, when it is required to set the operating parameters of the auto-darkening filter 20, the operator presses the key 90 first by his/her finger to unlock the touchable operating screen 40 such that it is back-lightened. For instance, in order to adjust the SHADE, the operator can press the SHADE mark by the finger such that the SHADE mark is enabled to shine itself and thus be in an activated state. Then, the finger can press the up or down adjusting arrow to alter the shade level correspondingly.

It is appreciated that the touchable operating screen is described only with respect to one of possible embodiments. The person skilled in the art can make any modification or alternation to the displaying or working manner of the graphics, icons or texts of the touchable operating screen.

In order to provide intuitional indication for the operator, the above mentioned marks and/or arrows can be displayed as various colors, such as red, green or blue or the like, in the activated state.

Figure 5A:
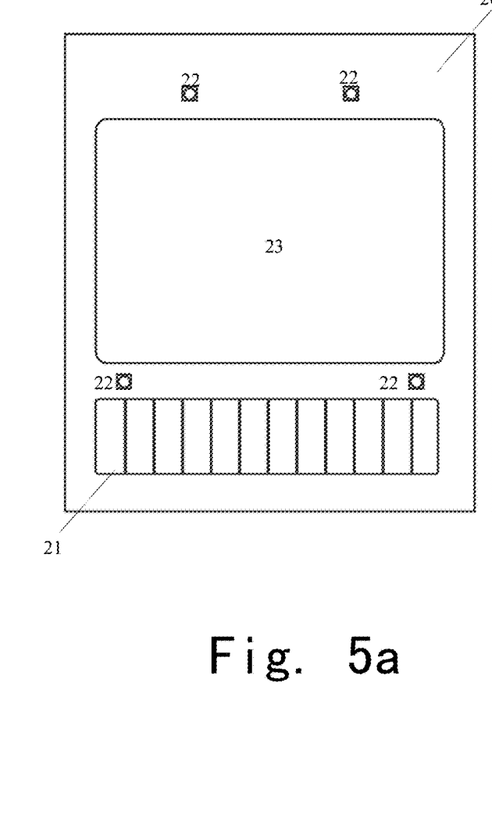
FIGS. 5a and 5b schematically show enlarged front and rear views of the auto-darkening filter equipped with a touchable operating screen according to another embodiment of the present application.
Figure 5B:
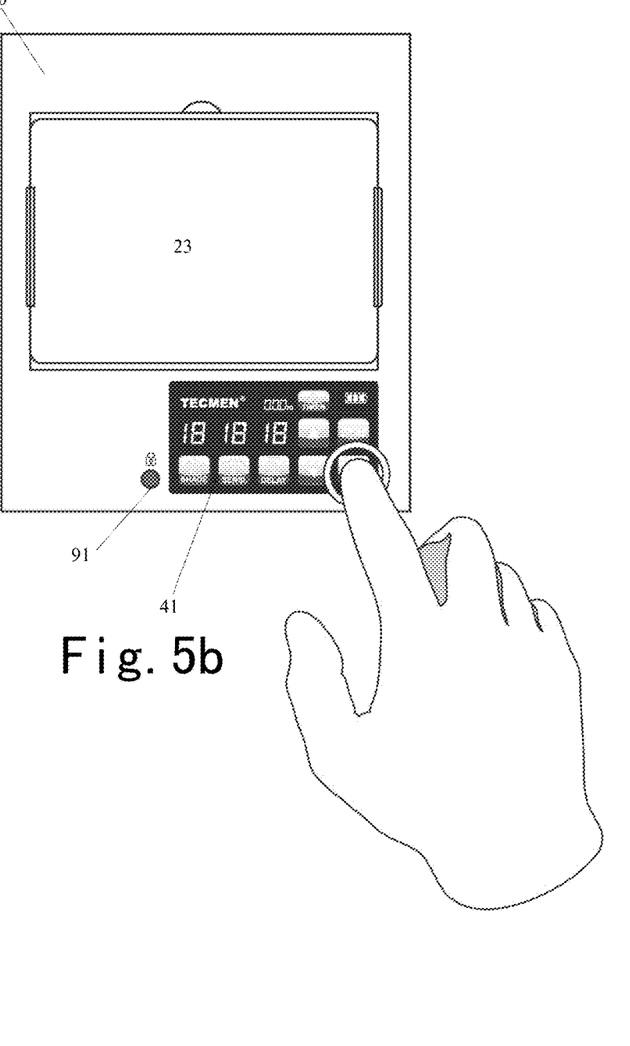

It should be noted that the design of the touchable operating screen 40 is not limited to the embodiment illustrated in FIG. 4*b*. For instance, FIGS. 5*a* and 5*b* show a touchable operating screen 41 according to another exemplary embodiment of the present application. This touchable operating screen 41 can be a cheaper monochromatic or black & white display screen. In this case, the marks and/or arrows can be designed to be selectively in a bright or dark state to indicate whether they are activated. In this embodiment, an "unlock/lock" key 91 is disposed on the body of the auto-darkening filter 20 under the liquid crystal panel 23 and aside the touchable operating screen 41. In this embodiment, the touchable operating screen 41 is designed to have a size smaller than the touchable operating screen 40, which thus leads to reduced manufacturing costs.

In the technical solutions of the present application, use of the touchable operating screen 40 or 41 is advantageous in that the operating parameters, the key, the marks or the like, which are displayed on the touchable screen, or their displaying manners can be modified as necessary. For instance, a "CONFIRM" key mark, a CUTTING operation manner mark or the like can be optionally added on the touchable operating screen 40 or 41. The former key mark can be used to make a confirmation after a level is selected by the finger. By comparison with the conventional mechanical adjustment device, the touchable operating screen according to the present application can be conveniently and rapidly upgraded by flexibly re-designing its operation interface at a later time.

When it is required to set the operating parameters of the welding helmet according to the present application, the operator should finish the following actions before he/she wears the welding helmet or after he/she takes off it from his/her head. That is to say, the operator should use one hand to support an outer side of the helmet housing or enable it to be placed on a bearing side such that his/her eyes face towards the inner surface of the helmet housing 10, especially towards the touchable operating screen, and then he/she can use the other hand to operate the screen.

In the described exemplary embodiments, the touchable operating screen is integrated into the body of the auto-darkening filter 20. However, it is understood by the skilled person in the art that in an alternative embodiment the touchable operating screen can be designed separately from the auto-darkening filter 20. For instance, the touchable operating screen can be installed onto the inner surface of the helmet housing 10 as an independent component. In this case, the independent touchable operating screen is connected, via an additional data cable, to the control circuit and the auto-darkening filter 20. This is advantageous in that the touchable operating screen can be disposed on the inner surface of the helmet housing 10 at a location where it can be readily operated by the operator, for example disposed on the inner surface of the helmet housing 10 at a location below the auto-darkening filter 20. Moreover, in this way, the size of the liquid crystal panel can be enlarged such that the outward visual field of the operator who wears the helmet can be broadened.

Although the specific embodiments of the present application have been explained in details, they are given only for illustrative purposes and cannot be thought to constitute any limitation to the present application. Any modification, change or combination to the embodiments described here which can be made by those skilled in the art after reading the present specification without departing from the spirit of the present application fall within the scope of the present application.

The invention claimed is:
1. An auto-darkening welding helmet, comprising:
a helmet housing;
a headband structure connected to the helmet housing;

an auto-darkening filter provided on the helmet housing, the auto-darkening filter comprising a liquid crystal panel; and a touchscreen configured to receive a touch input on the touchscreen to set operating parameters of the auto-darkening filter, wherein:

the touchscreen is disposed directly adjacent to the liquid crystal panel in the auto-darkening filter such that an operator can manipulate the touchscreen only when the auto-darkening welding helmet is not worn on a head of the operator, and the touchscreen faces towards the operator while the auto-darkening welding helmet is worn by the operator.

2. The auto-darkening welding helmet as recited in claim 1, wherein the touchscreen is integrated with the auto-darkening filter.

3. The auto-darkening welding helmet as recited in claim 1, wherein the touchscreen is provided on an inner surface of the helmet housing.

4. The auto-darkening welding helmet as recited in claim 2, wherein the touchscreen is located on a rear side of a body of the auto-darkening filter.

5. The auto-darkening welding welding helmet as recited in claim 1, wherein the operating parameters of the auto-darkening filter which are adjustable by the touchscreen comprise SHADE, SENSITIVITY, DELAY TIME, WELDING TIME, and operation modes including WELD, GRIND, and CUTTING.

6. The auto-darkening welding helmet as recited in claim 5, wherein the SHADE can be adjusted between 5 and 13 levels, the SENSITIVITY can be adjusted between 0 and 10 levels, and the DELAY TIME can be adjusted between 0 and 10 levels.

7. The auto-darkening welding helmet as recited in claim 1, wherein the touchscreen comprises a color display screen, a monochromatic display screen, or a black and white display screen.

8. The auto-darkening welding helmet as recited in claim 1, wherein the touchscreen is a resistance-type or capacitance-type touchable screen.

9. The auto-darkening welding helmet as recited in claim 1, wherein an "unlock/lock" key is provided on the auto-darkening filter such that the touchscreen can be activated in a working state or locked in a sleep state by pressing the "unlock/lock" key.

10. A method for manipulating an auto-darkening welding helmet, the method comprising:

receiving, via a touchscreen in the auto-darkening welding helmet, a touch input on the touchscreen from an operator; and in response to receiving the touch input, setting operating parameters of an auto-darkening filter of the auto-darkening welding helmet, wherein the auto-darkening welding helmet comprises:

a helmet housing, a headband structure connected to the helmet housing, the auto-darkening filter provided on the helmet housing, the auto-darkening filter comprising a liquid crystal panel, and the touchscreen configured to receive the touch input and disposed directly adjacent to the liquid crystal panel in the auto-darkening filter such that the touchscreen can be manipulated only when the auto-darkening welding helmet is not worn on a head of the operator.

11. The method of claim 10, wherein the touchscreen is integrated with the auto-darkening filter.

12. The method of claim 11, wherein the touchscreen is located on a rear side of a body of the auto-darkening filter.

13. The method of claim 10, wherein the touchscreen is provided on an inner surface of the helmet housing.

14. The method of claim 10, wherein the touchscreen comprises a color display screen, a monochromatic display screen, or a black and white display screen.

15. The method of claim 10, wherein the touchscreen is a resistance-type or capacitance-type touchable screen.

16. The method of claim 10, wherein an "unlock/lock" key is provided on the auto-darkening filter such that the touchscreen can be activated in a working state or locked in a sleep state by pressing the "unlock/lock" key.

17. The method of claim 10, wherein:

receiving the touch input from the operator comprises detecting the touch input on the touchscreen; and the touch input includes one of a sliding or pressing motion.

18. The auto-darkening welding helmet of claim 1, wherein:

the touchscreen is configured to receive the touch input by detecting the touch input on the touchscreen; and the touch input includes one of a sliding or pressing motion.

* * * * *